Oct. 31, 1972 K. M. SHEPHERD ET AL Re. 27,519

PACKAGE FOR STERILIZED ARTICLE

Original Filed Nov. 13, 1968

INVENTORS.
KENNETH M. SHEPHERD
RONALD L. WHIPPERMAN

BY Richard W. Carpenter
ATTORNEY.

aRO.

United States Patent Office

Re. 27,519
Reissued Oct. 31, 1972

27,519

PACKAGE FOR STERILIZED ARTICLE

Kenneth M. Shepherd, Prospect Heights, and Ronald L. Whipperman, North Chicago, Ill., assignors to Container Corporation of America, Chicago, Ill.

Original No. 3,527,400, dated Sept. 8, 1970, Ser. No. 775,345, Nov. 13, 1968. Application for reissue Mar. 10, 1971, Ser. No. 122,840

Int. Cl. B65d *33/16*

U.S. Cl. 229—87 R 2 Claims

Matter enclosed in heavy brackets [ ] appears in the original patent but forms no part of this reissue specification; matter printed in italics indicates the additions made by reissue.

ABSTRACT OF THE DISCLOSURE

A package, formed from a blank of foldable paperboard, has top and bottom panels adapted to be folded into a face-to-face relationship to enclose an article to be positioned therebetween. The bottom panel has a coating compound applied to the inner surface thereof while the inner surface of the top panel has flexible material secured thereto. The flexible material is sealed to the coated surface along predetermined lines of seal when the panels are folded to enclose the article. A portion of the coating compound on the inner surface of the bottom panel is releasable from that surface in the areas of the lines of seal upon opening of the package so that it adheres to the flexible material at the lines of seal and is pulled away from the bottom panel without tearing the paperboard and thereby preventing contamination of the article by loose particles of torn paperboard.

BACKGROUND OF THE INVENTION

Field of the invention

This invention relates to packages for confining sterilized articles therein and, more particularly, to packages formed from foldable blank of paperboard, or the like, and specifically adapted for confinement of sterilized articles therein.

The prior art

Card-like packages, formed from a blank of paperboard by sealing two foldably interconnected portions thereof to each other and sandwiching an article, such as a surgical instrument, therebetween are well known in the art. Normally, the article contained in the package has to be maintained in sterilized condition and is to be prevented from contacting any foreign elements which may destroy such condition. In opening packages known in the prior art, the paperboard is normally torn in breaking the seal between the two portions of the folded paperboard. Tearing of the paperboard produces particles of paper which may come into contact with the sterilized article thereby contaminating the article and preventing its safe use in designated medical functions.

SUMMARY OF THE INVENTION

The present invention overcomes the disadvantages found in the prior art and provides a package for a sterilized article, the sterilization of which is not affected by merely opening the package.

Generally, the package is formed from a blank of foldable paperboard which has top and bottom panels interconnected along a fold line so as to be folded into a face-to-face relationship with each other enclosing an article therebetween. The inner surface of the bottom panel is coated with a compound while the inner surface of the top panel has a flexible material attached thereto. When an article is placed in the package, the two panels are sealed to one another along predetermined lines of seal in such a way that the flexible material engages the coating on the inner surface of the bottom panel. When the package is opened, a portion of the coating adheres to the flexible material and is released from the inner surface of the bottom panel. The adherence takes place along the lines of seal with a portion of the compound being pulled away from the bottom panel without tearing the paperboard and thus preventing contamination of the article by loose particles of torn paperboard.

DRAWING

SPECIFICATION

Figure 1:
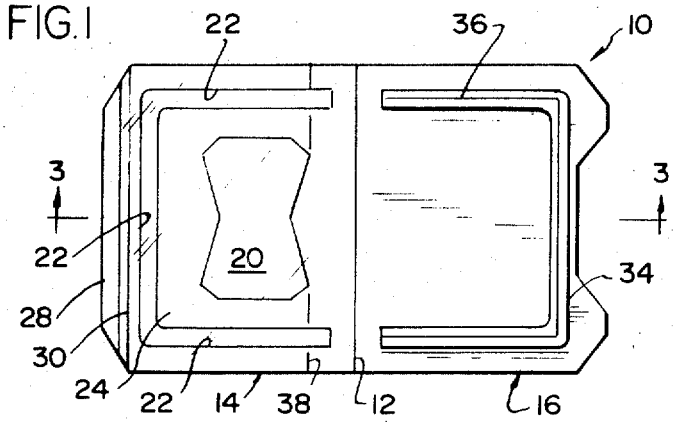
FIG. 1 is a plan view of a blank of paperboard from which one embodiment of the package of the present invention is formed.

While this invention is susceptible of embodiment in many different forms, there are shown in the drawing and will herein be described in detail, embodiments of the invention with the understanding that the present disclosure is to be considered as an exemplification of the principles of the invention and is not intended to limit the invention to the embodiments illustrated. The scope of the invention will be pointed out in the appended claims.

Referring now to the drawing, more specifically to FIG. 1, there is shown a blank of paperboard, generally designated 10. The blank is divided by a transverse fold line 12 which separates a top panel 14 from a bottom panel 16. The top panel 14 is formed with a central aperture 20 and seal line openings 22 which form a substantially U-shaped configuration.

Figure 3:
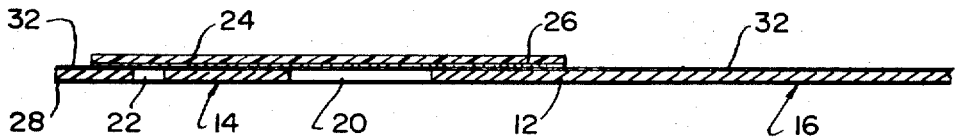
FIG. 3 is a sectional view, on an enlarged scale, taken generally along the line 3—3 of FIG. 1.
Figure 4:
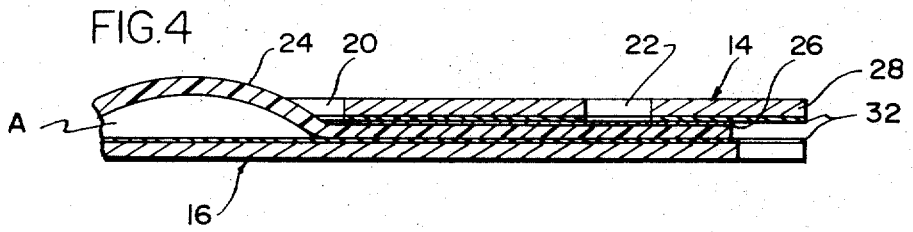
FIG. 4 is a sectional view on an enlarged scale, of a closed package formed from blank shown in FIG. 1.

A sheet of flexible material 24, such as a transparent film, is secured to the inner surface of the top panel 14 by adhesive 26, as indicated in FIG. 3, or by other known means. A pull tab 28, used for opening the package in a more convenient manner, is formed at the outer edge of the top panel 14 and separated from the main top panel by a score line 30. Prior to the application of film 24 to the inner surface of panel 14, the surface may be coated with a coating compound, as best indicated at 32 in FIG. 3, the compound including clay as one of its elements. The same coating compound 32 is applied to the inner surface of the bottom panel 16, as best indicated in FIG. 3. If desired, the bottom panel 16 may be formed with embossments 34 which correspond to the lines of seal and which come into registry with seal-line openings 22 in the top panel 14 when the panels are folded about the fold line 12 to be brought into a face-to-face relationship with one another and sealed along the lines of seal enclosing an article A therebetween. Further, the areas along the lines of seal have a tampering indicator, such as a colored line 36 marked with heat or pressure sensitive coloring, such as ink or paint.

For example, the line 36 may appear to be light blue in color before the package is sealed. Because of the sensitivity of the coloring to pressure or heat, the color of the line will turn to dark blue when the seal is made. Subsequently, if the seal is tampered with or broken, so as to expose a portion of the color line 36 to the atmosphere, the color of the line will again turn from dark blue to light blue to readily indicate to an observer that the package has an improper seal.

When the package is sealed along the lines of seal corresponding to openings 22 in the panel 14 to confine an article, the film 24 engages the coating compound 32 on the inner surface of the bottom panel 16 in the areas of the lines of seal. The article confined in the package might have been sterilized prior to placement thereof into the package. After the package has been sealed, the entire package may be sterilized by gas or steam sterilization or the like, to insure that the article remains in a sterile condition.

When the package is opened, a portion of the coating compound 32 applied to the inner surface of the bottom panel 16 is released therefrom and adheres to the flexible material, or film, 24 in the areas of the lines of seal. Since only a portion of the compound adheres to the film 24 at the lines of seal and is pulled away from the bottom panel 16, the remainder of the compound is retained on the panel 16 and prevents tearing of the paperboard along the lines of seal. Elimination of tearing of paperboard prevents occurrence of loose particles of paperboard which could come into contact with the sterilized article and thus contaminate the same making it unsafe for future intended use.

The coating compound serves yet another purpose in that it provides a surface which is more susceptible to accurate and aesthetically acceptable printing.

Figure 5:
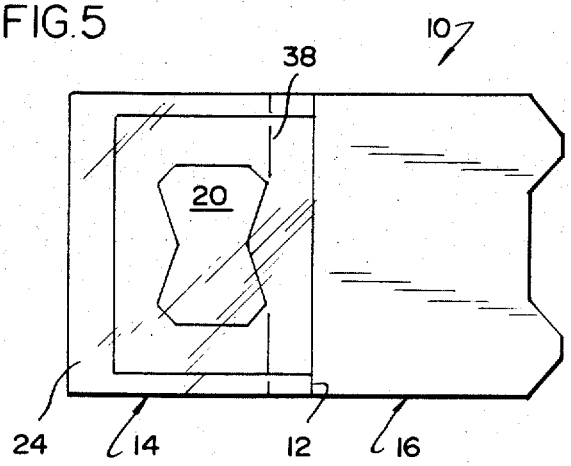
FIG. 5 is a plan view of a blank which another embodiment of the package of the present invention may be formed.
Figure 6:
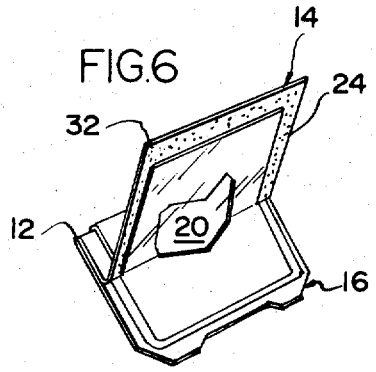
FIG. 6 is a perspective view of an open package formed from the blank shown in FIG. 5.

The other embodiment of the present invention, illustrated in FIGS. 5 and 6, is quite similar to the embodiment heretofore described so as to eliminate the need of detailed description of individual elements of the other embodiment. As best seen in FIGS. 5 and 6, a smaller paperboard portion of the top panel 14 is used with the flexible material, or film, 24 being adhesively, or otherwise, attached to the inner surface thereof to overlie the entire panel. The seal-line openings 22, present in the first embodiment, are eliminated from the present embodiment.

Figure 2:
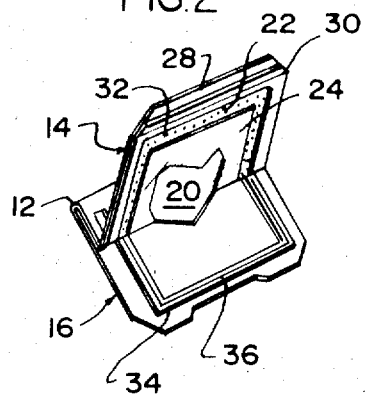
FIG. 2 is a perspective view of an opened package formed from a blank of FIG. 1.

The sealing and opening characteristics of the embodiment shown in FIGS. 5 and 6 is identical to that heretofore described in relation to the embodiment illustrated in FIGS. 1 through 3.

To prevent accidental dropping of the article from the opened package, the top panel 14 may be peeled back only to a line 38, as indicated in FIGS. 2 and 6. By so doing, one end of the article may be retained between the panels 14 and 16 in the unopened portion of the package to insure retention of the article in the package until removed therefrom by the user.

We claim:

1. A package, formed from [a blank of foldable] paperboard, for confining an article in a sterile condition, comprising:

(a) top and bottom panels [interconnected along a transverse fold line and foldable into] *disposed in* a face-to-face relationship with each other to enclose an article therebetween;

(b) said bottom panel having a coated inner surface formed by application of partially removable coating thereon;

(c) said top panel having an aperture and a sheet of flexible material secured to the inner surface of said top panel and extending across said aperture;

(d) said flexible material being sealed to said coated surface along predetermined lines of seal when said panels are *in face to face relationship* [folded] to enclose the article;

(e) a portion of said coating being released from said inner surface of said bottom panel at said lines of seal upon opening of the package so that said portion adheres to said flexible material and is pulled away from said bottom panel;

(f) the remaining portion of said coating being retained on said bottom panel at said lines of seal so as to avoid tearing of paperboard during opening of the package and prevent contamination of the article by loose particles of torn paperboard.

2. A package as defined in claim 1, wherein a tampering indicator is provided at said lines of seal and comprises a pressure sensitive color applied directly on said lines and adapted to undergo a change in color when the seal is broken.

References Cited

The following references, cited by the Examiner, are of record in the patented file of this patent or the original patent.

UNITED STATES PATENTS

| | | | |
|---|---|---|---|
| 2,554,035 | 5/1951 | Kreyling | 156—291 |
| 2,996,236 | 8/1961 | Barr | 229—40 |
| 3,078,182 | 2/1963 | Crone | 117—68.5 |

DONALD F. NORTON, Primary Examiner

U.S. Cl. X.R.

206—63.2 R; 229—3.5 R, 1.5 R